United States Patent [19]
Kajiyama et al.

[11] Patent Number: 5,330,906
[45] Date of Patent: Jul. 19, 1994

[54] MUTANT LUCIFERASE OF A FIREFLY

[75] Inventors: Naoki Kajiyama; Eiichi Nakano, both of Noda, Japan

[73] Assignee: Kikkoman Corporation, Japan

[21] Appl. No.: 76,042

[22] Filed: Jun. 15, 1993

Related U.S. Application Data

[62] Division of Ser. No. 675,211, Mar. 26, 1991, Pat. No. 5,219,737.

[30] Foreign Application Priority Data

Mar. 27, 1990 [JP] Japan ................................. 2-75696
Oct. 30, 1990 [JP] Japan ................................. 2-294258

[51] Int. Cl.$^5$ ..................... C12N 9/02; C12N 15/53; C12N 15/70
[52] U.S. Cl. ..................... 435/189; 435/71.2; 435/172.3; 435/252.3; 435/252.33; 435/320.1; 935/10; 935/14; 935/27; 935/56; 536/23.2
[58] Field of Search ............... 435/189, 71.2, 172.3, 435/252.3, 252.33, 320.1; 935/10, 14, 27, 56; 536/23.2

[56] References Cited

U.S. PATENT DOCUMENTS

| | | | |
|---|---|---|---|
| 4,320,195 | 3/1982 | Hill et al. | 435/55 |
| 4,743,561 | 3/1985 | Shaffer | 436/501 |

FOREIGN PATENT DOCUMENTS

| | | |
|---|---|---|
| 0301541 | 7/1988 | European Pat. Off. . |
| 0353464 | 2/1990 | European Pat. Off. . |

OTHER PUBLICATIONS

Masuda et al. Gene 77:265-270 (1989).
Chu et al. Virology 98:161-181 (1979).
DeWet et al. Mol. Cell. Biol 7:725-737 (Feb. 1987).
DeWet et al., 1985, Proc. Natl. Acad. Sci, USA, 82:7870-7873.
Wood et al., 1989, Science, 244:700-702.
Wood et al., 1989, J. Bioluminescence and Chemiluminescence 4:289-301.
Wood et al., 1989, J. Bioluminescence and Chemiluminescence 4:31-39.
Wood, J. Bioluminescence and Chemiluminescence 5:107-114 (Paper associated with talk presented at: Symposium on Lux Genes: Basic, Applications and Commercial Prospects, Cambridge, U.K., Dec., 1989).

*Primary Examiner*—Charles L. Patterson, Jr.
*Assistant Examiner*—Rebecca Prouty
*Attorney, Agent, or Firm*—Pennie & Edmonds

[57] ABSTRACT

The present invention provides industrially useful luciferase. Mutant luciferase of the invention is produced by culturing a microorganism belonging to the genus Escherichia which harbors a recombinant DNA containing the mutant luciferase gene of a firefly. Mutant luciferase can produce red, orange or green color of light which can not be produced by wild type luciferase. Mutant luciferase can be used to measure ATP accurately in a colored solution such as red (e.g., blood), orange, or green in which wild-type luciferase has not provided reliable results.

5 Claims, 2 Drawing Sheets

MUTANT LUCIFERASE OF A FIREFLY

This is a division of application Ser. No. 07/675,211, filed Mar. 26, 1991, now U.S. Pat. No. 5,219,737.

FIELD OF THE INVENTION

The present invention relates to mutant luciferase of a firefly, mutant luciferase genes thereof, recombinant DNAs containing the genes and a method of production for the mutant luciferase.

PRIOR ART

Firefly luciferase has been isolated from various fireflies such as *Luciola cruciata, Luciola lateralis, Photinus pyralis* and the like. Luciferase catalyzes luciferin to produce the olive green color (wave length: around 560 nm) of light. There has been no report on firefly luciferase which produces colors of light other than olive green.

Problems To Be Solved By The Invention

When the amount of ATP in a colored solution (e.g., blood) is to be determined by using wild type firefly luciferase, the sensitivity of the measurement is extremely impaired by the color of solution.

Means To Solve The Problem

The present inventors previously investigated on firefly luciferase which produced various colors of light other than olive green, and found that a transformant belonging to the genus Escherichia and carrying a recombinant luciferase DNA can produce colors of light such as red, orange, etc. (Japanese Patent Appln. No. 75696/1990).

We have further investigated on firefly luciferase which produces additional colors of light. We have successfully prepared a mutant capable of producing red, orange and green colors of light by isolating a wild type luciferase gene, inserting the gene into a vector, treating the construct with mutagens, transforming the genus Escherichia with the mutant, culturing the transformant in a medium, and recovering mutant luciferase producing a green color of light.

The present invention comprises the follows:

(1) A method of producing a mutant luciferase gene by treating a wild type luciferase gene of a firefly with a mutagen.

(2) A method of (1) wherein said mutant luciferase gene encodes mutant luciferase catalyzing luciferin to produce red, orange, or green color of light, different from the one produced by native luciferase.

(3) A mutant luciferase gene encoding the amino acid sequence of luciferase in which valine is replaced by isoleucine at the amino acid number 233, valine by isoleucine at 239, serine by asparagine at 286, glycine by serine at 326, histidine by tyrosine at 433 or proline by serine at 452.

(4) A recombinant DNA comprising the mutant luciferase genes of (3).

(5) A method of producing mutant luciferase of a firefly which comprises culturing in a medium a microorganism belonging to the genus Escherichia transformed with a recombinant DNA containing a mutant gene encoding the amino acid sequence of luciferase in which valine is replaced by isoleucine at the amino acid number 233, valine by isoleucine at 239, serine by asparagine at 286, glycine by serine at 326, histidine by tyrosine at 433, proline by serine at 452, and recovering mutant luciferase from the culture.

(6) Mutant luciferase having the amino acid sequence in which valine is replaced by isoleucine at the amino acid number 233, valine by isoleucine at 239, serine by asparagine at 286, glycine by serine at 326, histidine by tyrosine at 433, proline by serine at 452 in the sequence of native luciferase.

The invention is further illustrated in detail as follows:

Any luciferase gene of a firefly may be used, for example *Luciola cruciata, Luciola lateralis, Photinus pyralis* and the like. A wild type luciferase gene of a firefly is mutagenized to produce mutant luciferase genes. In mutagenesis of a wild type luciferase gene, a wild type luciferase gene alone may be mutagenized or a wild type luciferase gene is inserted in a vector (e.g., plasmid, bacteriophage) and then the construct is mutagenized.

A wild type luciferase gene of *Luciola cruciata* and its recombinant DNA can be obtained by the method described in the Japanese Patent Appln. LOP Publication No. 51086/1989. A wild type luciferase gene of *Luciola lateralis* and its recombinant DNA can be obtained by the method described in the Japanese Patent Appln. LOP Publication No. 322029/1988.

A wild type luciferase gene of a firefly or a recombinant DNA containing the gene is treated with mutagens such as hydroxylamine, N-methyl-N-nitro-N-nitrosoguanidine, nitrous acid, sulfurous acid, hydrazine, formic acid or 5-bromouracil. Though any concentration of a mutagen may be used, 0.5–12M is preferable. The treatment may be carried out at 20°–80° C. for more than 10 minutes, preferably 10–180 minutes. Alternatively, a wild type luciferase gene of a firefly or a recombinant DNA containing the gene may be exposed to UV light for 10–60 minutes. Chemically or enzymatically synthesized oligonucleotides may be also utilized.

The mutant genes thus obtained are inserted into a vector such as plasmid or bacteriophage (Japanese Patent Appln. LOP Publication No. 51086/1989, Japanese Patent Appln. No. 322029/1988) according to the method known in the art. The constructs are used to transform a microorganism belonging to the genus Escherichia such as *E. coli* JM101 (ATCC 33876), DH1 (ATCC 33849) and HB101 (ATCC 33694) according to the method described by Hanahan, 1985, DNA Cloning, 1: 109–135. Alternatively, the constructs are used for transduction according to the method (Molecular Cloning, 1982, Cold Spring Harbor Laboratory).

The transformants and transductants are screened for the production of mutant luciferase. A transformant capable of producing mutant luciferase is selected.

Purified recombinant DNA is obtained from the transformant according to the method described by Guerry, P., 1973, J. Bacteriology, 116: 1064–1066 and Clewell, D. B., 1972, J. Bacteriology, 110: 667–676.

The DNA fragment containing the mutant luciferase gene can be obtained from the recombinant DNA using restriction enzymes such as EcoRI and PstI. The reaction mixture is incubated at 30°–40° C. for 1–24 hours, preferably at 37° C. for 2 hours. After digestion, the mixture is electrophoresed on an agarose gel according to the method (Molecular Cloning, 1982, Cold Spring Harbor Laboratory).

The nucleotide sequence of a mutant luciferase gene can be determined according to the method as described in Section 17 of Example.

The transformants capable of producing mutant luciferase may be cultured in a solid medium, but a liquid culture medium is preferable.

Suitable medium includes more than one nitrogen source among yeast extract, tryptone, peptone, meat extract, corn steep liquor and exudate of soybean or wheat, and more than one inorganic salt among NaCl, potassium dihydrogen phosphate, dipotassium hydrogen phosphate, magnesium sulfate, magnesium chloride, ferric chloride, ferric sulfate, manganese sulfate and the like, and if necessary, some carbohydrates and vitamins.

The pH of the culture medium is preferably adjusted to 7-9. Incubation may be carried out at 30°-42° C. for 4-24 hours, preferably 37° C. for 6-8 hours in a submerged aeration culture, a shaking culture, or a stationary culture.

After incubation, mutant luciferase is recovered from the culture according to the methods known in the art: Mutant luciferase is recovered by disrupting cells using sonication, mechanical and enzymatic (e.g., lysozyme) lysis or by incubating cells in the presence of toluene with or without shaking and allowing cells to secrete enzyme into the medium. The lysate is filtered or centrifuged to remove cells and cell debris. If it is necessary to remove nucleic acid, streptomycin sulfate, protamine sulfate or manganese sulfate was added to the filtrate or the supernatant. The mixture is then fractionated using ammonium sulfate, alcohol or acetone. The precipitate recovered contains crude luciferase.

Crude enzyme thus obtained may be purified by a method or the combination of methods which includes a gel filtration method using Sephadex, Ultro-Gel or Bio-Gel, adsorption chromatography using an ion-exchanger or hydroxyapatite, affinity chromatography, polyacrylamide gel electrophoresis, sucrose density gradient centrifugation, and fractional filtration using a molecular sieve and hollow fiber membrane.

Purified luciferase is characterized as follows: Mutant luciferase catalyzes luciferin to produce colors of light, orange (wavelength: 595 nm and 607 nm), red (609 nm and 612 nm) and green (558 nm). The other physical and chemical properties of mutant luciferase of *Luciora cruciata* are found identical to those of native luciferase as described in the Japanese Patent Appln. LOP Publication No. 141592/1989. Similarly, the other physical and chemical properties of mutant luciferase of Luciora lateralis found identical to those of native luciferase (Japanese Patent Appln. LOP Publication No. 262791/1989).

The Effect of the Invention

The present invention provides industrially useful luciferase. Mutant luciferase of the invention is produced by culturing a microorganism belonging to the genus Escherichia which carries the recombinant DNA containing the mutant luciferase gene of a firefly. Mutant luciferase can produce red, orange and green colors of light which are not seen by native luciferase. Mutant luciferase can be used to measure ATP accurately in a colored solution such as red (e.g., blood), orange, or green colors in which native luciferase has not provided reliable results.

EXAMPLE

Figure 1:
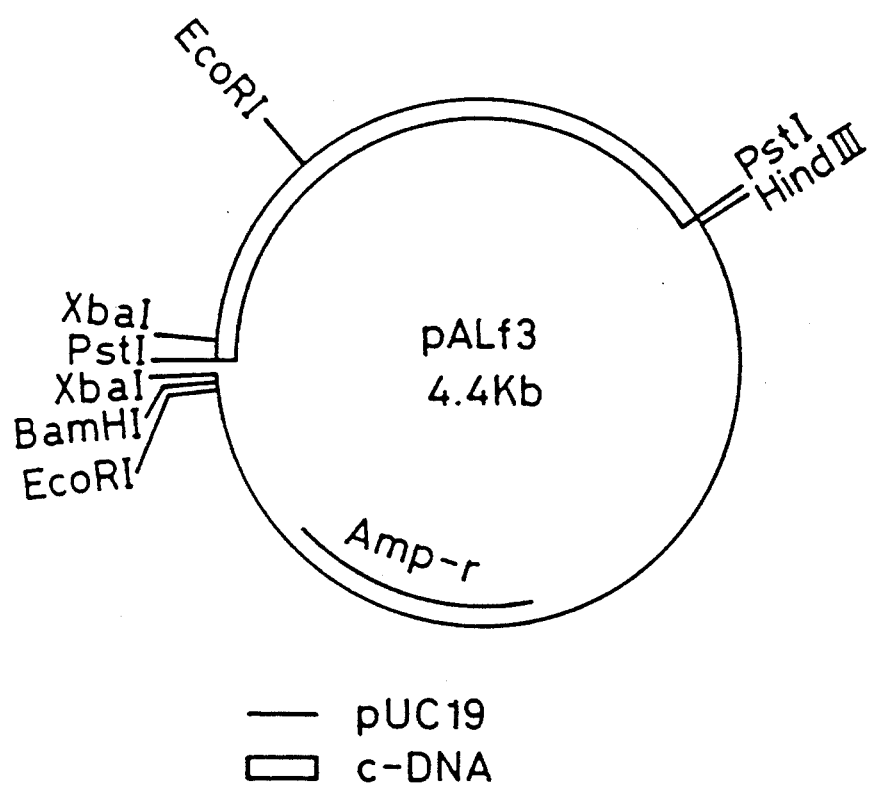
FIG. 1 shows the restriction map of a recombinant plasmid pALf3.

The following example further illustrates the invention.

The following Sections 1-10 describe the construction of a recombinant DNA containing the luciferase cDNA of *Photinus pyralis* (*Photinus pyralis* is a member of fireflies). The construct is used as a probe to screen the luciferase gene of *Luciora cruciata*.

(1) Preparation of a Luciferase mRNA of *Photinus pyralis*

1 g of dried tails of *Photinus pyralis* (Sigma) was ground well using a mortar and a pestle. 5 ml of buffer [20 mM Tris-HCl/pH 7.4, 10 mM NaCl, 3 mM magnesium acetate, 5% (w/v) sucrose, 1.2% (v/v) Triton X-100, 10 mM vanadyl nucleoside complex (New England Biolabs)] was added to the material. The material was further ground as described above.

5 ml of the solution thus obtained was placed in a blender cup (Nippon Seiki Seisakusho Co.) and mixed at 5,000 r.p.m. for 5 minutes. 12 ml of a guanidine isothiocyanate solution [6 M guanidine isothiocyanate, 37.5 mM sodium citrate/pH 7.0, 0.75% (w/v) sodium N-lauroylsarcosinate, 0.15 M $\beta$-mercaptoethanol] was added to the mixture. The mixture was mixed in a blender cup at 3,000 r.p.m. for 10 minutes. Then, the mixture was filtrated through a three-folded gauze. The filtrate was layered onto four ultracentrifuge tubes (Hitachi Koki Co.) containing 1.2 ml each of 5.7M cesium chloride. The tube was ultracentrifuged (SCP55H, Hitachi Koki Co.) at 30,000 for 16 hours at 15° C. The precipitate was washed with ice cold 70% (v/v) ethanol and resuspended in 4 ml of 10 mM Tris buffer (10 mM Tris-HCl/pH 7.4, 5 mM EDTA, 1% sodium dodecylsulfate). The mixture was extracted with an equal volume of a n-butanol/chloroform (4:1 v/v) mixture. The extract was centrifuged at 3,000 r.p.m. for 10 minutes. The aqueous phase was saved and 4 ml of 10 mM Tris buffer was added to the organic phase. The organic phase was back-extracted 2x and the aqueous phase was pooled each time. To the combined aqueous phase, 1/10 volume of 3M sodium acetate/pH 5.2 and two volumes of ice cold ethanol were added. The mixture was incubated at $-20°$ C. for 2 hours. After incubation, the mixture was centrifuged at 8,000 r.p.m. for 20 minutes. The RNA precipitate was removed and dissolved in 4 ml of water. RNA was precipitated with ethanol and resuspended in 1 ml of water. 3.75 mg of RNA was obtained.

The above procedure was repeated and a total amount of RNA recovered was 7 mg. mRNA was separated from total RNA using an oligo (dT) cellulose (New England Biolabs) column chromatography. The oligo (dT) column was prepared by filling a 2.5 ml Terumo syringe column (Terumo Co.) with 0.5 g of resin which had previously been swelled in an elution buffer [10 mM Tris-HCl/pH 7.6, 1 mM EDTA, 0.1% (w/v) sodium dodecylsulfate]. The column was then equilibrated with binding buffer [10 mM Tris-HCl/pH 7.6, 1 mM EDTA, 0.4M NaCl, 0.1% sodium dodecylsulfate].

An equal volume of buffer [10 mM Tris-HCl/pH 7.6, 1 mM EDTA, 0.8M NaCl, 0.1% sodium dodecylsulfate] was added to the RNA (7 mg) suspension. The mixture was incubated at 65° C. for 10 minutes, cooled on ice, and loaded on the oligo (dT) cellulose column. The column was then washed with binding buffer to remove unbound rRNA and tRNA. Elution buffer was loaded on the top of the column to elute mRNA. 40 μg of mRNA was obtained.

(2) Isolation of Luciferase mRNA mRNA was concentrated using a sucrose density gradient centrifugation. The sucrose gradient was made as follows: 0.5 ml of 40% (w/v) sucrose [50 mM Tris-HCl/pH 7.5, 20 mM NaCl, 1 mM EDTA, 40% (w/v) sucrose] was placed in a polyaroma tube (Beckman rotor SW41). Then, 2.4 ml of each sucrose (25% (w/v), 20% (w/v), 15% (w/v), 10% (w/v)) was layered. The gradient was left standing at 4° C. for 24 hours. 30 μg of mRNA was layered onto the sucrose gradient. The tube was ultracentrifuged at 30,000 r.p.m. at 18° C. for 18 hours. After centrifugation, a total volume was removed in a 0.5 ml fraction. Ethanol was added to each fraction. The precipitate was removed and resuspended in 10 μl of water.

The fraction containing a high level of luciferase mRNA was selected as follows: 1 μl of the fraction, 9 μl of rabbit reticulocyte lysate (Amersham) and 1 μl of $^{35}$S-methionine (Amersham) were combined. The mixture was incubated at 30° C. for 30 minutes. 150 μl of NET [150 mM NaCl, 5 mM EDTA, 0.02% (w/v) NaN$_3$, 20 mM Tris-HCl/pH 7.4, 0.05% (w/v) Nonidet P-40 (BRL detergent)] was added to the mixture. Then, 1 μl of anti-luciferase serum (prepared as described in Section 3) was added to the mixture. The mixture was incubated at 4° C. for 18 hours. 10 mg of Protein A Sepharose (Pharmacia) was added to the mixture. The mixture was incubated at 20° C. for 30 minutes. After incubation, the mixture was centrifuged at 12,000 r.p.m. for one minute. The pellet was recovered and washed 3x with 200 μl of NET. 40 μl of sample buffer [62.5 mM Tris-HCl/pH 6.8, 10% (v/v) glycerol, 2% (w/v) sodium dodecylsulfate, 5% (v/v) β-mercaptoethanol, 0.02% (w/v) Bromophenol Blue] was added to the pellet. The mixture was boiled at 100° C. for three minutes and centrifuged at 12,000 r.p.m. for one minute. The supernatant was loaded on 12% (w/v) SDS-PAGE. Electrophoresis was carried out according to the method (Laemmli, 1970, Nature p227, p680). After electrophoresis, the gel was immersed in 10% acetic acid for 30 minutes, washed in water for 30 minutes and immersed in 1M sodium salicylic acid for 30 minutes. The gel was dried and exposed to a X-ray film (Fuji Film Co.) for fluorography.

The film was analyzed: The presence of a band on the film indicated the presence of an elevated level of luciferase mRNA in that fraction.

(3) Preparation of Rabbit Anti-luciferase Serum

Rabbit antiserum against purified luciferase was prepared as follows.

0.7 ml of luciferase (3.2 mg/ml) [luciferase (Sigma) was dissolved in0.5M glycylglycine/pH 7.8] was mixed with an equal volume of Freund's complete adjuvant (2.24 mg). The mixture was injected to a pad of a Japanese white rabbit (2 kg). The rabbit was boosted two weeks after the first injection with the same amount of the antigen-adjuvant mixture intracutaneously at the back. One week later, the rabbit was boosted as described above. One week after the final injection, the rabbit was sacrificed and bled.

The blood was left standing at 4° C. for 18 hours and then centrifuged at 3,000 r.p.m. for 15 minutes to give a supernatant containing anti-luciferase serum.

(4) Preparation of a Luciferase cDNA

Luciferase cDNA was prepared using Amersham's kit.

cDNA was prepared from 2.0 μg of mRNA according to the method described in Mol. Cell. Biol. 2: 161, 1982 and Gene 25: 263, 1983, as recommended by the manufacturer's instructions.

150 ng of cDNA was suspended in 7 μl of TE (10 mM Tris-HCl/pH 7.5, 1 mM EDTA). 11 μl of buffer (280 mM sodium cacodylate/pH 6.8, 60 mM Tris-HCl/pH 6.8, 2 mM cobalt chloride), 3.8 μl of a tailing solution [7.5 μl of 10 mM dithiothreitol, 1 μl of poly A (10 ng/ml), 2 μl of 5 mM dCTP, 110 μl of water] and 29 units of terminal transferase (Boehringer Mannheim Inc.) were added to the suspension. The mixture was incubated at 30° C. for 10 minutes. After incubation, 2.4 μl of 0.25M EDTA and 2.4 [2l of 10% (w/v) sodium dodecylsulfate were added to the mixture to stop the reaction.

25 μl of phenol equilibrated with water was added to the mixture. The aqueous phase was saved. 25 μl of 4M ammonium acetate and 100 μl of ice cold ethanol were added to the aqueous portion. The mixture was incubated at −70° C. for 15 minutes. After incubation, the mixture was centrifuged at 12,000 r.p.m. for 10 minutes. The pellet was removed and resuspended in 10 μl of TE. The resulting suspension contained 100 ng of deoxycytidine-tailed cDNA.

(5) Preparation of a Vector pMCE10 pKN305 and pMC1403-3 (Japanese Patent Appln. LOP Publication No. 274683/1986) were constructed using E. coli W3110 (ATCC 27325), pBR325 (BRL), pBR322 (Takara Shuzo Co., LTD) according to the method described by Masuda, T. et. al., (1986, Agricultural Biological Chemistry 50: 271-279). 182 g of pKN304 DNA and 1 μg pMC1403-3 DNA were dissolved in 10 μl of a solution (50 mM Tris-HCl/pH 7.5, 10 mM MgCl$_2$, 100 mM NaCl, 1 mM dithiothreitol) in a separate tube. 2 units of HindIII and 2 units of SalI (Takara Shuzo Co., LTD) were added to each tube. The mixture was incubated at 37° C. for an hour. After digestion, the mixture was extracted with phenol. The extract was then precipitated with ethanol. The precipitate was dissolved in 10 μl of ligation buffer (20 mM MgCl$_2$, 60 mMTris-HCl/pH 7.6, 1 mM ATP, 15 mM dithiothreitol). 1 unit of T4 DNA ligase (Takara Shuzo Co., LTD) was added to the solution and the mixture was incubated at 20° C. for 4 hours. The mixture was used to transform JM101 (ATCC 33876) according to the method (J. Bacteriology, 1974, 119: 1072-1074). The transformants were screened on an agar plate containing ampicillin and tetracycline in addition to a necessary culture medium. The transformants were then further screened for the β-galactocidase activity. After screening, a positive colony was found and designated JM101 (pMCE10). The recombinant plasmid contained was designated pMCE10. JM101 (pMCE10) was cultured at 37° C. for 16-24 hours. 20 ml of the culture was added to 1 l of a culture medium [1% (w/v) tryptone, 0.5% (w/v) yeast extract, 0.5% (w/v) NaCl]. The mixture was incubated at 37° C. for three hours. At three hours of incubation, 0.2 g of chloramphenicol was added to the mixture. The mixture was further incubated at 37° C. for 20 hours.

The culture was centrifuged at 6,000 r.p.m. for 10 minutes to give 2 g of the cells which were suspended in 20 ml of 350 mM Tris-HCl/pH 8.0 buffer containing 25% (w/v) sucrose. 10 mg of lysozyme, 8 ml of 0.25M EDTA/pH 8.0 and 8 ml of 20% (w/v) sodium dodecylsulfate were added to the suspension. The mixture was incubated at 60° C. for 30 minutes.

13 ml of 5M NaCl was then added to the mixture. The mixture was further incubated at 4° C. for 16 hours. After incubation, the mixture was centrifuged at 15,000 r.p.m. for 30 minutes. The supernatant was extracted with phenol. Then, DNA was precipitated with ethanol.

The precipitate was dried under reduced pressure and then dissolved in 6 ml of TE. 6 g of cesium chloride and 0.2 ml (10 mg/ml) of ethidium bromide were added to the solution. The mixture was ultracentrifuged at 39,000 r.p.m. for 42 hours. After centrifugation, pMCE10 DNA portion was removed and extracted with n-butanol to remove ethidium bromide. The DNA solution was then dialyzed against TE. After dialysis, the dialysate contained 500 µg of DNA.

(6) Preparation of Deoxyguanidine-tailed Vector pMCE10 and pUC19

15 µg of pMCE10 was dissolved in 90 µl of TE. 10 µl of Med buffer [100 mM Tris-HCl/pH 7.5, 100 mM $MgCl_2$, 10 mM dithiothreitol, 500 mM NaCl ] and 30 units of AccI (Takara Shuzo Co., LTD) were added to the solution. The mixture was incubated at 37° C. for an hour. After digestion, the mixture was extracted with 100 µl of phenol equilibrated with water. To the extract, 1/10 volume of 3M sodium acetate/pH 7.5 and two volumes of ice cold ethanol were added. The mixture was incubated at −70° C. for 15 minutes. After incubation, the mixture was centrifuged at 12,000 r.p.m. for 10 minutes. The pellet was resuspended in 10 µl of TE.

15 µl of a solution (280 mM sodium cacodylate/pH 6.8, 60 mM Tris-HCl/pH 6.8, 2 mM cobalt chloride), 5 µl of a tailing solution [7.5 µl of 10 mM dithiothreitol, 1 µl of poly A (10 ng/ml), 2 µl of 5 mM dGTP, 110 µl of water] and 5 units of terminal transferase (Takara Shuzo Co., LTD) were added to the mixture. The mixture was incubated at 37° C. for 15 minutes. The rest of the procedure was carried out as described in Section 4. The resulting solution contained DNA of pMCE10 with a deoxyguanosine tail at the AccI site.

DNA of pUC19 with a deoxyguanosine tail at the PstI site was prepared as follows: 30 µg of pUC19 (Takara Shuzo Co., LTD) was dissolved in 350 µl of TE. 40 µl of Med buffer and 120 units of PstI (Takara Shuzo Co., LTD) were added to the solution. The mixture was incubated at 37° C. for an hour. After digestion, the mixture was extracted with phenol. Then, DNA was precipitated with ethanol.

The precipitate was then resuspended in 35 µl of TE. 50 µl of a solution (280 mM sodium cacodylate/pH 6.8, 60 mM Tris-HCl/pH 6.8, 1 mM cobalt chloride), 19 µl of a tailing solution (described above, containing dGTP) and 60 units of terminal transferase (Takara Shuzo Co., LTD) were added to the suspension. The mixture was incubated at 37° C. for 10 minutes. After incubation, the mixture was extracted with phenol. DNA was then recovered by ethanol precipitation.

(7) Construction of a Luciferase cDNA Library 15 ng of deoxycytidine-tailed luciferase cDNA and 200 ng of deoxyguanidine-tailed pMCE10 were dissolved in 35 µl of annealing buffer (10 mM Tris-HCl/pH 7.5, 100 mM NaCl, 1 mM EDTA) in a tube. Similarly, 15 ng of deoxycytidine-tailed luciferase cDNA and 200 ng of deoxyguanidine-tailed pUC19 were dissolved in 35 µl of annealing buffer in a tube. The tubes were heated at 65° C. for 2 minutes, at 46° C. for 2 hours, at 37° C. for an hour, and then at 20° C. for 18 hours.

The constructs (recombinant plasmids of pMCE10 and pUC19, which contain luciferase cDNA) were used to transform E. coli DH1 (ATCC 33849) according to the method described by Hanahan (1985, DNA Cloning, 1: 109–135).

(8) Screening of the Luciferase cDNA Library

The AccI site of pMCE10 was located in the coding region of a β-galactosidase gene. The luciferase cDNA of pMCE10 produced a fusion protein bound to β-galactosidase. The promoter of the β-galactosidase gene of pMCE10 had been replaced by that of the tryptophan gene of E. coli as described previously.

96 colonies of the luciferase cDNA library in the pMCE10 vector were incubated with shaking in 10 ml of a M9 casamino acid medium (Maniatis, T., 1982, Molecular Cloning, Cold Spring Harbor Laboratory, N.Y., pp 440–441) containing 10 µg/ml of thiamin at 37° C. for 10 hours. After incubation, the bacterial cells were harvested. The cells were suspended in 200 µl of sample buffer (see Section 2). The suspension was boiled at 100° C. for 5 minutes.

40 µl of the suspension was electrophoresed on a 7.5% (w/v) polyacrylamide gel. After electrophoresis, proteins on the gel were transferred to a nitrocellulose filter according to the western blot analysis (Anal. Biochem. 112: 195, 1981). The nitrocellulose filter was treated with anti-luciferase serum using an immunoblot assay kit (Bio-Rad) according to the method recommended by the manufacturer's instructions: The filter was immersed in 100 ml of a blocking solution [TBS (20 mM Tris-HCl, 500 mM NaCl/pH 7.5) containing 3% (w/v) gelatin] and incubated with shaking at 25° C. for 30 minutes. The filter was then transferred to 25 ml of a primary antibody solution [anti-luciferase serum was diluted 1:25 v/v with TBS containing 1% (w/v) gelatin] and incubated with shaking at 25° C. for 90 minutes. The filter was transferred to 100 ml of Tween-20 Wash [TBS containing 0.05% (w/v) Tween-20] and incubated with shaking at 25° C. for 10 minutes. This washing procedure was repeated one more time. The filter was transferred to 60 ml of a secondary antibody solution [horseradish peroxidase labelled anti-rabbit antibody (Bio-Rad) diluted 1:3000 (v/v) with TBS containing 1% (w/v) gelatin] and incubated with shaking at 25° C. for 60 minutes. The filter was washed 2x with 100 ml of Tween-20 Wash. The filter was then transferred to 120 ml of a staining solution and incubated at 25° C. for 10 minutes. The staining solution was prepared as follows: 60 mg of 4-chloro-1-naphthol was dissolved in 20 ml of cold methanol (solution A). 60 µl of 30% (v/v) hydrogen peroxide was added to 100 ml of TBS (solution B). The solution A and B were combined.

Manipulating 96 colonies as a set, we screened additional three sets of colonies as described above. Two sets were positive. The two sets were further tested: The two sets of colonies were divided into 16 groups (12 colonies per group). The 16 groups were screened as described above. Of these, two groups were positive. 24 colonies were then screened individually as described above. Of these, two positive colonies were found and plasmid DNA of the two colonies was prepared as described in Section 5. The plasmid DNAs were designated pALf2B8 and pALf3A6.

(9) Preparation of a DNA Probe for the Screening of the Luciferase cDNA Library

100 μg of pALf3A6 DNA was dissolved in 330 μl of TE. 40 μl of low buffer (100 mM Tris-HCl/pH 7.5, 100 mM MgCl$_2$, 10 mM dithiothreitol), 130 units of PstI (Takara Shuzo Co., LTD) and 120 units of SacI (Boehringer Mannheim) were added to the solution. The mixture was incubated at 37° C. for 1.5 hours.

Digested DNA was electrophoresed on a 0.7% (w/v) agarose gel according to the method described by Maniatis, T., (1984, Molecular Cloning, pp 156–161, Cold Spring Harbor Laboratory, N.Y.). The band containing the luciferase cDNA was cut out and placed in a dialysis tube. 2 ml of TE was added to the tube and the tube was sealed. The tube was subjected to electroelution. The DNA solution was removed from the tube and extracted with an equal volume of phenol equilibrated with water. DNA was precipitated with ethanol.

10 μg of DNA thus obtained was resuspended in 126 μl of TE. 16 μl of Med buffer and 64 units of Sau3AI (Takara Shuzo Co., LTD) were added to the suspension. The mixture was incubated at 37° C. for 2 hours. After digestion, the restriction fragments were electrophoresed on a 5% (w/v) polyacrylamide gel according to the method described by Maxam, A. (1980, Methods in Enzymology 65: 506). 1 μg of the 190 bp Sau3AI fragment containing the luciferase cDNA was isolated as described above.

1 μg of the fragment was labelled with α-$^{32}$P-dCTP (Amersham) using a kit (Takara Shuzo Co., LTD) according to the nick translation method (J. Mol. Biol., 1977, 113: 237–251 and Molecular Cloning, 1982, Cold Spring Harbor Laboratory, N.Y., pp 109–112).

(10) Screening of the Luciferase cDNA Library in the pUC19 Vector Using the $^{32}$P-Labelled Probe The luciferase cDNA library in the pUC19 vector was screened using the $^{32}$P-labelled probe according to the colony hybridization method (Proteins, Nucleic Acid, Enzyme, 1981, 26: 575–579). Positive colonies were obtained and one of colonies was designated as pALf3. pALf3 DNA was prepared as described in Section 5 and used to transform E. coli DH1. The transformant was designated as DH1 (pALf3). DH1 (pALf3) was deposited as ATCC 67462.

pALf3 DNA was digested with one or two enzymes from the group consisting of XbaI, HindIII, BamHI, EcoRI and PstI (Takara Shuzo Co., LTD). For a molecular weight marker, λDNA (Takara Shuzo Co., LTD) was digested with HindIII. The restriction fragments were electrophoresed on an agarose gel. The band patterns of digested pALf3 DNA were compared with those of the λDNA marker. The size of the luciferase cDNA fragment was found to be 1,700 bp. The restriction map of pALf3 is shown in FIG. 1.

(11) Preparation of Luciferase mRNA of *Luciola cruciata*

10 g of living Luciola cruciata (purchased from Seibu Department Store) was placed in an ultracold freezer. After the insect was frozen they were taken out from the freezer. The tails of fireflies were cut off with scissors to yield 2 g of the tails. 18 ml of a guanidine isothiocyanate solution was added to 2 g of the tails. 1.1 mg of total RNA was recovered and loaded onto the top of an oligo (dT) cellulose column according to the method as described in Section 1. 30 μg of luciferase mRNA was recovered.

(12) Construction of the Luciferase cDNA Library of *Luciola cruciata* cDNA was prepared using a kit (Amersham) according to the method (Mol. Cell. Biol., 1982, 2: 161 and Gene, 1983, 25: 263).

0.9 μg of double-stranded cDNA was prepared from 2 μg of mRNA. 0.3 μg of cDNA was polydeoxycytidine-tailed according to the method as described in Section 4.

20 ng of polydeoxycytidine-tailed cDNA and 500 ng of polydeoxyguanocine-tailed pUC19 DNA (see Section 6) were annealed according to the method as described in Section 7. The construct was used to transform E. coli DH1 (ATCC 33849) according to the method described by Hanahan (1985, DNA Cloning, 1: 109–135).

(13) Screening of the Luciferase cDNA Library

Figure 2:
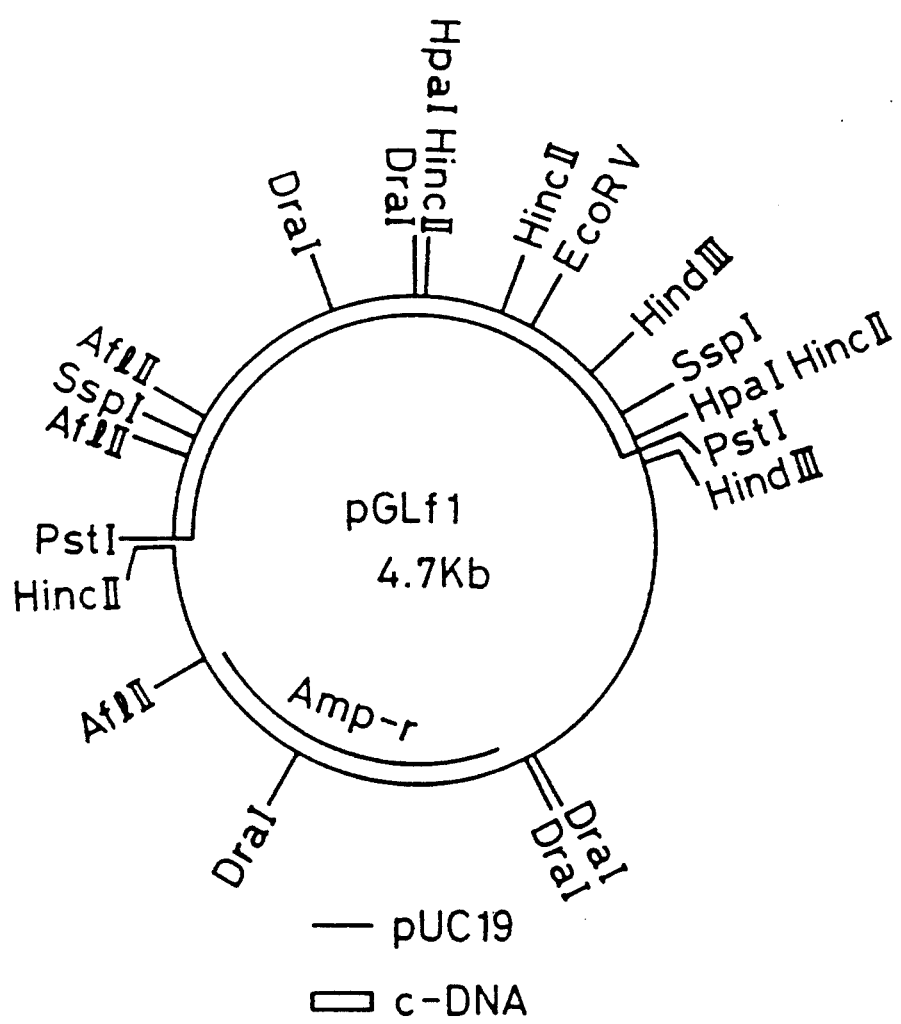
FIG. 2 shows the restriction map of a recombinant plasmid pGLf1.

10 μg of pALf3 DNA as described in Section 10 was dissolved in 90 μl of TE. 10 μl of Med buffer, 25 units each of EcoRI and ClaI (Takara Shuzo Co., LTD) were added to the solution. The mixture was incubated at 37° C. for 2 hours. After digestion, the restriction fragments were electrophoresed on an agarose gel. The 800 bp EcoRI-ClaI fragment containing luciferase cDNA was isolated. 1 μg of the DNA fragment recovered was labelled with α-$^{32}$P-dCTP (Amersham) according to the nick translation method. The luciferase cDNA library of *Luciora cruciata* was screened using the $^{32}$P-labelled probe according to the colony hybridization method. Several positive colonies were obtained and one of the colonies was designated at pGLf1. pGLf1 DNA was prepared according to the method as described in Section 5, and used to transform E. coli DH1. The transformant was designated as DH1 (pGLf1). DH1 (pGLf1) was deposited as ATCC 67482.

pGLf1 DNA was digested with one or two enzymes from the group consisting of HpaI, HindIII, EcoRV, DraI, AflII, HincII, PstI (Takara Shuzo Co., LTD) and SspI (New England Bio-Laboratory). For a molecular weight marker, λ phage DNA (Takara Shuzo Co., LTD) was digested with HindIII. The restriction fragments were electrophoresed on an agarose gel. The band patterns were analyzed. The fragment containing luciferase cDNA was 2,000 bp. The restriction map of pGLf1 is shown in FIG. 2.

(14) DNA Sequencing of the Luciferase cDNA of *Luciola cruciata*

10 μg of pGLf1 DNA was digested with PstI (Takara Shuzo Co., LTD). After digestion, 2.5 μg of the 2.0 kb DNA fragment containing the luciferase cDNA was recovered. The 2.0 kb fragment was inserted into the PstI site of pUC119 (Takara Shuzo Co., LTD). The constructs were designated as pGLf2 and pGLf3 according to the orientation of the inserted fragment.

The recombinant plasmids pGLf2 and pGLf3 were constructed as follows:

pGLf1 DNA and pUV119 DNA were digested with PstI according to the method as described in Section 6. The luciferase cDNA fragment was isolated by agarose gel electrophoresis according to the method as described in Section 9. The restriction fragments of the vector and the insert were ligated according to the method as described in Section 5. JM101 (ATCC 33876) was transformed with the constructs according to the method as described in Section 5. DNA of pGLf2 and pGLf3 was prepared according to the method as in Section 5.

Various deletion mutations were introduced into pGLf2 and pGLf3 using a kilosequence deletion kit (Takara Shuzo Co., LTD) according to the method described by Henikoff (1984, Gene 28: 351-359). E. coli JM101 (ATCC 33876) was then transformed with the deletion mutants of pGLf2 and pGLf3. The transformants were infected with a helper phage M13K07 (Takara Shuzo Co., LTD) to prepare single-stranded DNA according to the method described by Messing (1983, Methods in Enzymology, 101: 20-78). Single-stranded DNA was sequenced using a M13 sequencing kit (Takara Shuzo Co., LTD) according to the method (Messing, see above). Sequencing was carried out on a polyacrylamide gel (Fuji Film Co., LTD).

The nucleotide sequence of the luciferase cDNA of *Luciora cruciata* is shown in the Sequence Listing SEQ ID: No. 1. The amino acid sequence deduced from the nucleotide sequence is shown in the Sequence Listing SEQ ID: No. 2.

(15) Construction of a Recombinant Plasmid pGLf37

The 4.0 kb DNA fragment containing most of the vector segment as well as the luciferase cDNA lacking 27 nucleotides at the N-terminal was prepared as follows:

1 µg of pGLf1 DNA was dissolved in 90 µl of water. 10 µl of Med buffer and 20 units of PstI (Takara Shuzo Co., LTD) were added to the solution. The mixture was incubated at 37° C. for 2 hours. After digestion, an equal volume of phenol equilibrated with water was added to the mixture. The DNA fragments were recovered by ethanol precipitation, and inserted into a vector. The constructs were used to transform *E. coli* JM101 (ATCC 33876), and plasmid DNA was prepared from the transformants according to the method as in Section 5.

Plasmid DNA of the transformants was digested with one or two enzymes from the group consisting of SspI, EcoRV and PstI. The construct containing the cDNA fragment in the orientation opposite to the one in pGLf1 was designated as pGLf10.

10 µg of pGLf10 DNA was dissolved in 90 µl of water. 10 µl of Med buffer and 10 units of SspI (New England Bio-Lab) were added to the solution. The mixture was incubated at 37° C. for 30 minutes. After partial digestion, the 4.0 kb DNA fragment (2 µg) containing most of the vector segment as well as the luciferase cDNA lacking 27 nucleotides at the N-terminal was recovered.

1 µg of the 4.0 kb DNA fragment was dissolved in 95 µl of water. 5 µl of 1M Tris-HCl/pH 8.0 and 1 µl (0.3 unit) of alkaline phosphatase (Takara Shuzo Co., LTD) were added to the solution. The mixture was incubated at 65° C. for an hour. After dephosphorylation, the mixture was extracted with phenol. Then, DNA was precipitated with ethanol. 1 µg of the 4.0 kb DNA fragment dephosphorylated at both ends was recovered.

The DNA fragment containing the trp promoter of *E. coli* was prepared as follows:

10 µg of pKN206 DNA containing a trp promoter (Agric. Biol. Chem. 1986, 50: 271-279) was dissolved in 90 µl of water. 10 µl of Med buffer and 20 units of ClaI (Takara Shuzo Co., LTD) were added to the solution and the mixture was incubated at 37° C. for 2 hours. After complete digestion, the restriction fragments were further digested with 10 units of SspI at 37° C. for 30 minutes. After partial digestion with SspI, the DNA fragments were extracted with phenol. Then, DNA was precipitated with ethanol. The precipitate was resuspended in 100 µl of TE. The 500 bp DNA fragment containing almost all the trp promoter was isolated according to the method described in Section 9.

Oligonucleotides for the 4.0 kb fragment and the trp promoter were synthesized as follows:

The luciferase cDNA of the 4.0 kb DNA fragment lacked the nucleotide sequence encoding nine amino acids at N-terminal according to the nucleotide sequence analysis. The trp promoter of the 500 bp DNA fragment lacked part of the sequence between the SD region and the ATG initiation codon. To fill the missing sequences of the 4.0 kb DNA fragment and the trp promoter, two oligonucleotides as defined in the Sequence Listing by SEQ: ID Nos. 3 and 4 were synthesized using a System 1 Plus DNA synthesizer (Beckman).

The oligomers were purified using a NENSORB PREP (Dupont) and 20 µg of each oligomer was recovered. 1 µg each of the purified oligomers was dissolved in 45 µl of water in a separate tube. 5 µl of 10× kination buffer (0.5M Tris-HCl/pH 7.6, 0.1M $MgCl_2$, 50 mM dithiothreitol, 10 mM ATP) and 1 µl (10 unit) of T4 polynucleotide kinase (Takara Shuzo Co., LTD) were added to the tubes. The mixtures were incubated at 37° C. for an hour. The mixtures were extracted with phenol. Then, DNA was precipitated with ethanol. 1 µg each of the oligomer phosphorylated at the 5' end was recovered.

A recombinant plasmid pGLf37 was constructed as follows:

1 µg of the 4.0 kb fragment, 1 µg of the 500 bp fragment and 0.1 µg each of the oligomer phosphorylated as above were dissolved in 8 µl of water. 1 µl of 10× ligation buffer (200 mM $MgCl_2$, 660 mM Tris-HCl/pH 7.6, 10 mMATP, 150 mM dithiothreitol) and 1 µl (1 unit) of T4 DNA ligase (Takara Shuzo Co., LTD) were added to the mixture. The mixture was incubated at 16° C. for 16 hours. Then, the mixture was used for transformation. Transformation of JM101 (ATCC 33876) and isolation of plasmid DNA were carried out in an analogous way as in Section 5. Plasmid DNA was digested with one or two enzymes from the group consisting of SspI, EcoRV and PstI. The restriction fragments were electrophoresed on a 0.7% agarose gel. The recombinant plasmid containing the trp promoter and the luciferase cDNA was selected and designated as pGLf37. A JM101 transformant carrying pGLf37 was designated as JM101 (pGLf37).

(16) Mutagenesis of Recombinant Plasmid pGLf37

30 µg of pGLf37 DNA was dissolved in 100 µl of a hydroxylamine solution (0.8M hydroxylamine hydrochloride, 0.1M phosphate buffer/pH 6.8, 1 mM EDTA). The mixture was incubated at 65° C. for 2 hours. After incubation, DNA was precipitated with ethanol in conventional way. The precipitate was resuspended in TE (10 mM Tris-HCl/pH 7.5, 1 mM EDTA). The mixture was used to transform E- coli JM101 (ATCC 33876) according to the method described by Hanahan (1985, DNA Cloning, 1: 109-135). The mixture containing the transformants was plated out on an LB-amp agar plate [1% (w/v) bactotrypton, 0.5% (w/v) yeast extract, 0.5% (w/v) NaCl, 50 μg/ml of ampicillin, 1.4% (w/v) agar]. The plate was incubated at 37° C. for 12 hours. A colony appeared on the plate was inoculated into 3 ml of an LB-amp medium [1% (w/v) bactotrypton, 0.5% (w/v) yeast extract, 0.5% (w/v) NaCl, 50 μg/ml of ampicillin] and incubated with shaking at 37° C. for 18 hours. 0.5 ml of the culture was added to 10 ml of an LB-amp medium. The mixture was incubated with shaking at 37° C. for 4 hours. After incubation, the mixture was centrifuged at 8,000 r.p.m. for 10 minutes.

20 mg of the cells collected was suspended in 0.9 ml of a buffer (0.1M $KH_2PO_4$/pH 7.8, 2 mM EDTA, 1 mM dithiothreitol, 0.2 mg/ml of protamine sulfate). 100 μl of lysozyme solution (10 mg/ml) was added to the suspension. The mixture was placed on ice for 15 minutes. The mixture was then frozen in a dry ice/methanol bath. The mixture was removed from the bath and left standing at 25° C. When the mixture was completely thawed, it was centrifuged at 12,000 r.p.m. for 5 minutes. 1 ml of a supernatant containing crude enzyme was obtained.

50 μl of the crude enzyme solution thus obtained was added to 400 μl of a luciferin/ATP mixture [260 μl of 25 mM glycylglycine/pH 7.8, 16 μl of 0.1M magnesium sulfate, 24 μl of 1 mM luciferin (Sigma), 100 μl of 10 mM ATP] to observe the color of the light. There were six types of colors: red (609 nm and 612 nm), orange (595, 607), green (two 558's).

Alternatively, crude enzyme was purified according to the method described in the Japanese Patent Appln. LOP Publication No. 141592/1989, tested, and found the same color displayed as described above.

Recombinant DNAs encoding mutant luciferase which produces red colors of light (609 nm and 612 nm) were designated as pGLf37C-M-2 and pGLf37C-M-5, respectively. E. coli JM101 was transformed with pGLf37C-M-2 or pGLf37C-M-5. The transformants, E. coli JM101 (pGLf37C-M-2) and JM101 (pGLf37C-M-5) were deposited with Fermentation Research Institute, Agency of Industrial Science and Technology and were assigned the accession number FERM BP-2825 and FERM BP-3136, respectively. Recombinant DNAs encoding mutant luciferase which produces orange colors of light (595 nm and 607 nm) were designated as pGLf37C-M-4 and pGLf37C-M-1, respectively. The transformants, E. coli JM101 (pGLf37C-M-4) and JM101 (pGLf37C-M-1), were deposited with the same and were assigned the accession number FERM BP-2826 and FERM BP-3135, respectively. Recombinant DNAs encoding mutant luciferase which produces green colors of light (two wavelengths of 558 nm) were designated as pGLf37C-M-6 and pGLf37C-M-7, respectively. The transformants, E. coli JM101 (pGLf37C-M-6) or JM101 (pGLf37C-M-7), were deposited with the same and were assigned the accession number FERM BP-3137 and FERM BP-3138, respectively.

Table I summarizes the color of light, the position of mutation in the nucleotide sequence and the position of mutation in the amino acid sequence of the bacterial strains.

TABLE I

| Bacterial Strains | Color of Light (wavelength) | Base Substitution & its Position | Amino Acid Substitution & its Position |
|---|---|---|---|
| E. coli JM101 (pGLf37C-M-2) | Red (609 nm) | G → A 976 | Gly → Ser 326 |
| E. coli JM101 (pGLf37C-M-5) | Red (612 nm) | C → T 1297 | His → Tyr 433 |
| E. coli JM101 (pGLf37C-M-4) | Orange (595 nm) | C → T 1354 | Pro → Ser 452 |
| E. coli JM101 (pGLf37C-M-1) | Orange (607 nm) | G → A 857 | Ser → Asn 286 |
| E. coli JM101 (pGLf37C-M-6) | Green (558 nm) | G → A 715 | Val → Ile 239 |
| E. coli JM101 (pGLf37C-M-7) | Green (558 nm) | G → A 697 | Val → Ile 233 |

What is claimed is:

1. A mutant luciferase having the amino acid sequence of the luciferase of *Luciola cruciata* in which one of the following changes appears: serine is replaced by asparagine at amino acid 286, glycine is replaced by serine at amino acid 326, histidine is replaced by tyrosine at amino acid 433 or proline is replaced by serine at amino acid 452.

2. The mutant luciferase according to claim 1, in which serine is replaced by asparagine at amino acid 286.

3. The mutant luciferase according to claim 1, in which glycine is replaced by serine at amino acid 326.

4. The mutant luciferase according to claim 1, in which histidine is replaced by tyrosine at amino acid 433.

5. The mutant luciferase according to claim 1, in which proline is replaced by serine at amino acid 452.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1644 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Luciola cruciata ( i x ) FEATURE:
        ( A ) NAME/KEY: CDS
        ( B ) LOCATION: 1..1644

( x i ) SEQUENCE DESCRIPTION: SEQ ID NO:1:

```
ATG GAA AAC ATG GAA AAC GAT GAA AAT ATT GTA GTT GGA CCT AAA CCG        48
Met Glu Asn Met Glu Asn Asp Glu Asn Ile Val Val Gly Pro Lys Pro
 1               5                  10                  15

TTT TAC CCT ATC GAA GAG GGA TCT GCT GGA ACA CAA TTA CGC AAA TAC        96
```

-continued

| | | | | | | | | | | | | | | |
|---|---|---|---|---|---|---|---|---|---|---|---|---|---|---|
|Phe|Tyr|Pro|Ile|Glu|Glu|Gly|Ser|Ala|Gly|Thr|Gln|Leu|Arg|Lys|Tyr|
| | |20| | | |25| | | |  |30| | | |

| ATG | GAG | CGA | TAT | GCA | AAA | CTT | GGC | GCA | ATT | GCT | TTT | ACA | AAT | GCA | GTT | 144 |
|---|---|---|---|---|---|---|---|---|---|---|---|---|---|---|---|---|
| Met | Glu | Arg | Tyr | Ala | Lys | Leu | Gly | Ala | Ile | Ala | Phe | Thr | Asn | Ala | Val | |
| | | 35 | | | | 40 | | | | 45 | | | | | | |

| ACT | GGT | GTT | GAT | TAT | TCT | TAC | GCC | GAA | TAC | TTG | GAG | AAA | TCA | TGT | TGT | 192 |
|---|---|---|---|---|---|---|---|---|---|---|---|---|---|---|---|---|
| Thr | Gly | Val | Asp | Tyr | Ser | Tyr | Ala | Glu | Tyr | Leu | Glu | Lys | Ser | Cys | Cys | |
| | | 50 | | | | 55 | | | | 60 | | | | | | |

| CTA | GGA | AAA | GCT | TTG | CAA | AAT | TAT | GGT | TTG | GTT | GTT | GAT | GGC | AGA | ATT | 240 |
|---|---|---|---|---|---|---|---|---|---|---|---|---|---|---|---|---|
| Leu | Gly | Lys | Ala | Leu | Gln | Asn | Tyr | Gly | Leu | Val | Val | Asp | Gly | Arg | Ile | |
| 65 | | | | | 70 | | | | | 75 | | | | | 80 | |

| GCG | TTA | TGC | AGT | GAA | AAC | TGT | GAA | GAA | TTT | TTT | ATT | CCT | GTA | ATA | GCC | 288 |
|---|---|---|---|---|---|---|---|---|---|---|---|---|---|---|---|---|
| Ala | Leu | Cys | Ser | Glu | Asn | Cys | Glu | Glu | Phe | Phe | Ile | Pro | Val | Ile | Ala | |
| | | | | 85 | | | | 90 | | | | | 95 | | | |

| GGA | CTG | TTT | ATA | GGT | GTA | GGT | GTT | GCA | CCC | ACT | AAT | GAG | ATT | TAC | ACT | 336 |
|---|---|---|---|---|---|---|---|---|---|---|---|---|---|---|---|---|
| Gly | Leu | Phe | Ile | Gly | Val | Gly | Val | Ala | Pro | Thr | Asn | Glu | Ile | Tyr | Thr | |
| | | | 100 | | | | | 105 | | | | | 110 | | | |

| TTA | CGT | GAA | CTG | GTT | CAC | AGT | TTA | GGT | ATC | TCT | AAA | CCA | ACA | ATT | GTA | 384 |
|---|---|---|---|---|---|---|---|---|---|---|---|---|---|---|---|---|
| Leu | Arg | Glu | Leu | Val | His | Ser | Leu | Gly | Ile | Ser | Lys | Pro | Thr | Ile | Val | |
| | | | 115 | | | | | 120 | | | | | 125 | | | |

| TTT | AGT | TCT | AAA | AAA | GGC | TTA | GAT | AAA | GTT | ATA | ACA | GTA | CAG | AAA | ACA | 432 |
|---|---|---|---|---|---|---|---|---|---|---|---|---|---|---|---|---|
| Phe | Ser | Ser | Lys | Lys | Gly | Leu | Asp | Lys | Val | Ile | Thr | Val | Gln | Lys | Thr | |
| | 130 | | | | | 135 | | | | | 140 | | | | | |

| GTA | ACT | ACT | ATT | AAA | ACC | ATT | GTT | ATA | CTA | GAT | AGC | AAA | GTT | GAT | TAT | 480 |
|---|---|---|---|---|---|---|---|---|---|---|---|---|---|---|---|---|
| Val | Thr | Thr | Ile | Lys | Thr | Ile | Val | Ile | Leu | Asp | Ser | Lys | Val | Asp | Tyr | |
| 145 | | | | | 150 | | | | | 155 | | | | | 160 | |

| CGA | GGA | TAT | CAA | TGT | CTG | GAC | ACC | TTT | ATA | AAA | AGA | AAC | ACT | CCA | CCA | 528 |
|---|---|---|---|---|---|---|---|---|---|---|---|---|---|---|---|---|
| Arg | Gly | Tyr | Gln | Cys | Leu | Asp | Thr | Phe | Ile | Lys | Arg | Asn | Thr | Pro | Pro | |
| | | | | 165 | | | | | 170 | | | | | 175 | | |

| GGT | TTT | CAA | GCA | TCC | AGT | TTC | AAA | ACT | GTG | GAA | GTT | GAC | CGT | AAA | GAA | 576 |
|---|---|---|---|---|---|---|---|---|---|---|---|---|---|---|---|---|
| Gly | Phe | Gln | Ala | Ser | Ser | Phe | Lys | Thr | Val | Glu | Val | Asp | Arg | Lys | Glu | |
| | | | 180 | | | | | 185 | | | | | 190 | | | |

| CAA | GTT | GCT | CTT | ATA | ATG | AAC | TCT | TCG | GGT | TCT | ACC | GGT | TTG | CCA | AAA | 624 |
|---|---|---|---|---|---|---|---|---|---|---|---|---|---|---|---|---|
| Gln | Val | Ala | Leu | Ile | Met | Asn | Ser | Ser | Gly | Ser | Thr | Gly | Leu | Pro | Lys | |
| | | | 195 | | | | | 200 | | | | | 205 | | | |

| GGC | GTA | CAA | CTT | ACT | CAC | GAA | AAT | ACA | GTC | ACT | AGA | TTT | TCT | CAT | GCT | 672 |
|---|---|---|---|---|---|---|---|---|---|---|---|---|---|---|---|---|
| Gly | Val | Gln | Leu | Thr | His | Glu | Asn | Thr | Val | Thr | Arg | Phe | Ser | His | Ala | |
| | 210 | | | | | 215 | | | | | 220 | | | | | |

| AGA | GAT | CCG | ATT | TAT | GGT | AAC | CAA | GTT | TCA | CCA | GGC | ACC | GCT | GTT | TTA | 720 |
|---|---|---|---|---|---|---|---|---|---|---|---|---|---|---|---|---|
| Arg | Asp | Pro | Ile | Tyr | Gly | Asn | Gln | Val | Ser | Pro | Gly | Thr | Ala | Val | Leu | |
| 225 | | | | | 230 | | | | | 235 | | | | | 240 | |

| ACT | GTC | GTT | CCA | TTC | CAT | CAT | GGT | TTT | GGT | ATG | TTC | ACT | ACT | CTA | GGG | 768 |
|---|---|---|---|---|---|---|---|---|---|---|---|---|---|---|---|---|
| Thr | Val | Val | Pro | Phe | His | His | Gly | Phe | Gly | Met | Phe | Thr | Thr | Leu | Gly | |
| | | | | 245 | | | | | 250 | | | | | 255 | | |

| TAT | TTA | ATT | TGT | GGT | TTT | CGT | GTT | GTA | ATG | TTA | ACA | AAA | TTC | GAT | GAA | 816 |
|---|---|---|---|---|---|---|---|---|---|---|---|---|---|---|---|---|
| Tyr | Leu | Ile | Cys | Gly | Phe | Arg | Val | Val | Met | Leu | Thr | Lys | Phe | Asp | Glu | |
| | | | 260 | | | | | 265 | | | | | 270 | | | |

| GAA | ACA | TTT | TTA | AAA | ACT | CTA | CAA | GAT | TAT | AAA | TGT | ACA | AGT | GTT | ATT | 864 |
|---|---|---|---|---|---|---|---|---|---|---|---|---|---|---|---|---|
| Glu | Thr | Phe | Leu | Lys | Thr | Leu | Gln | Asp | Tyr | Lys | Cys | Thr | Ser | Val | Ile | |
| | | 275 | | | | | 280 | | | | | 285 | | | | |

| CTT | GTA | CCG | ACC | TTG | TTT | GCA | ATT | CTC | AAC | AAA | AGT | GAA | TTA | CTC | AAT | 912 |
|---|---|---|---|---|---|---|---|---|---|---|---|---|---|---|---|---|
| Leu | Val | Pro | Thr | Leu | Phe | Ala | Ile | Leu | Asn | Lys | Ser | Glu | Leu | Leu | Asn | |
| | 290 | | | | | 295 | | | | | 300 | | | | | |

| AAA | TAC | GAT | TTG | TCA | AAT | TTA | GTT | GAG | ATT | GCA | TCT | GGC | GGA | GCA | CCT | 960 |
|---|---|---|---|---|---|---|---|---|---|---|---|---|---|---|---|---|
| Lys | Tyr | Asp | Leu | Ser | Asn | Leu | Val | Glu | Ile | Ala | Ser | Gly | Gly | Ala | Pro | |
| 305 | | | | | 310 | | | | | 315 | | | | | 320 | |

| TTA | TCA | AAA | GAA | GTT | GGT | GAA | GCT | GTT | GCT | AGA | CGC | TTT | AAT | CTT | CCC | 1008 |
|---|---|---|---|---|---|---|---|---|---|---|---|---|---|---|---|---|
| Leu | Ser | Lys | Glu | Val | Gly | Glu | Ala | Val | Ala | Arg | Arg | Phe | Asn | Leu | Pro | |
| | | | | 325 | | | | | 330 | | | | | 335 | | |

| GGT | GTT | CGT | CAA | GGT | TAT | GGT | TTA | ACA | GAA | ACA | ACA | TCT | GCC | ATT | ATT | 1056 |
|---|---|---|---|---|---|---|---|---|---|---|---|---|---|---|---|---|
| Gly | Val | Arg | Gln | Gly | Tyr | Gly | Leu | Thr | Glu | Thr | Thr | Ser | Ala | Ile | Ile | |
| | | | 340 | | | | | 345 | | | | | 350 | | | |

| | | | | | | | | | | | | | | | | |
|---|---|---|---|---|---|---|---|---|---|---|---|---|---|---|---|---|
| ATT | ACA | CCA | GAA | GGA | GAC | GAT | AAA | CCA | GGA | GCT | TCT | GGA | AAA | GTC | GTG | 1104 |
| Ile | Thr | Pro | Glu | Gly | Asp | Asp | Lys | Pro | Gly | Ala | Ser | Gly | Lys | Val | Val | |
| | | 355 | | | | | 360 | | | | | 365 | | | | |
| CCG | TTG | TTT | AAA | GCA | AAA | GTT | ATT | GAT | CTT | GAT | ACC | AAA | AAA | TCT | TTA | 1152 |
| Pro | Leu | Phe | Lys | Ala | Lys | Val | Ile | Asp | Leu | Asp | Thr | Lys | Lys | Ser | Leu | |
| | | 370 | | | | 375 | | | | | 380 | | | | | |
| GGT | CCT | AAC | AGA | CGT | GGA | GAA | GTT | TGT | GTT | AAA | GGA | CCT | ATG | CTT | ATG | 1200 |
| Gly | Pro | Asn | Arg | Arg | Gly | Glu | Val | Cys | Val | Lys | Gly | Pro | Met | Leu | Met | |
| 385 | | | | | 390 | | | | | 395 | | | | | 400 | |
| AAA | GGT | TAT | GTA | AAT | AAT | CCA | GAA | GCA | ACA | AAA | GAA | CTT | ATT | GAC | GAA | 1248 |
| Lys | Gly | Tyr | Val | Asn | Asn | Pro | Glu | Ala | Thr | Lys | Glu | Leu | Ile | Asp | Glu | |
| | | | | 405 | | | | | 410 | | | | | 415 | | |
| GAA | GGT | TGG | CTG | CAC | ACC | GGA | GAT | ATT | GGA | TAT | TAT | GAT | GAA | GAA | AAA | 1296 |
| Glu | Gly | Trp | Leu | His | Thr | Gly | Asp | Ile | Gly | Tyr | Tyr | Asp | Glu | Glu | Lys | |
| | | | 420 | | | | | 425 | | | | | 430 | | | |
| CAT | TTC | TTT | ATT | GTC | GAT | CGT | TTG | AAG | TCT | TTA | ATC | AAA | TAC | AAA | GGA | 1344 |
| His | Phe | Phe | Ile | Val | Asp | Arg | Leu | Lys | Ser | Leu | Ile | Lys | Tyr | Lys | Gly | |
| | | 435 | | | | | 440 | | | | | 445 | | | | |
| TAC | CAA | GTA | CCA | CCT | GCC | GAA | TTA | GAA | TCC | GTT | CTT | TTG | CAA | CAT | CCA | 1392 |
| Tyr | Gln | Val | Pro | Pro | Ala | Glu | Leu | Glu | Ser | Val | Leu | Leu | Gln | His | Pro | |
| | 450 | | | | | 455 | | | | | 460 | | | | | |
| TCT | ATC | TTT | GAT | GCT | GGT | GTT | GCC | GGC | GTT | CCT | GAT | CCT | GTA | GCT | GGC | 1440 |
| Ser | Ile | Phe | Asp | Ala | Gly | Val | Ala | Gly | Val | Pro | Asp | Pro | Val | Ala | Gly | |
| 465 | | | | | 470 | | | | | 475 | | | | | 480 | |
| GAG | CTT | CCA | GGA | GCC | GTT | GTT | GTA | CTG | GAA | AGC | GGA | AAA | AAT | ATG | ACC | 1488 |
| Glu | Leu | Pro | Gly | Ala | Val | Val | Val | Leu | Glu | Ser | Gly | Lys | Asn | Met | Thr | |
| | | | | 485 | | | | | 490 | | | | | 495 | | |
| GAA | AAA | GAA | GTA | ATG | GAT | TAT | GTT | GCA | AGT | CAA | GTT | TCA | AAT | GCA | AAA | 1536 |
| Glu | Lys | Glu | Val | Met | Asp | Tyr | Val | Ala | Ser | Gln | Val | Ser | Asn | Ala | Lys | |
| | | | 500 | | | | | 505 | | | | | 510 | | | |
| CGT | TTA | CGT | GGT | GGT | GTT | CGT | TTT | GTG | GAT | GAA | GTA | CCT | AAA | GGT | CTT | 1584 |
| Arg | Leu | Arg | Gly | Gly | Val | Arg | Phe | Val | Asp | Glu | Val | Pro | Lys | Gly | Leu | |
| | | 515 | | | | | 520 | | | | | 525 | | | | |
| ACT | GGA | AAA | ATT | GAC | GGC | AGA | GCA | ATT | AGA | GAA | ATC | CTT | AAG | AAA | CCA | 1632 |
| Thr | Gly | Lys | Ile | Asp | Gly | Arg | Ala | Ile | Arg | Glu | Ile | Leu | Lys | Lys | Pro | |
| | 530 | | | | | 535 | | | | | 540 | | | | | |
| GTT | GCT | AAG | ATG | | | | | | | | | | | | | 1644 |
| Val | Ala | Lys | Met | | | | | | | | | | | | | |
| 545 | | | | | | | | | | | | | | | | |

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Luciola cruciata ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Asn | Met | Glu | Asn | Asp | Glu | Asn | Ile | Val | Val | Gly | Pro | Lys | Pro |
| 1 | | | | 5 | | | | | 10 | | | | | 15 | |
| Phe | Tyr | Pro | Ile | Glu | Glu | Gly | Ser | Ala | Gly | Thr | Gln | Leu | Arg | Lys | Tyr |
| | | | 20 | | | | | 25 | | | | | 30 | | |
| Met | Glu | Arg | Tyr | Ala | Lys | Leu | Gly | Ala | Ile | Ala | Phe | Thr | Asn | Ala | Val |
| | | 35 | | | | | 40 | | | | | 45 | | | |
| Thr | Gly | Val | Asp | Tyr | Ser | Tyr | Ala | Glu | Tyr | Leu | Glu | Lys | Ser | Cys | Cys |
| | 50 | | | | | 55 | | | | | 60 | | | | |
| Leu | Gly | Lys | Ala | Leu | Gln | Asn | Tyr | Gly | Leu | Val | Val | Asp | Gly | Arg | Ile |
| 65 | | | | | 70 | | | | | 75 | | | | | 80 |

-continued

| | | | | | | | | | | | | | | |
|---|---|---|---|---|---|---|---|---|---|---|---|---|---|---|
| Ala | Leu | Cys | Ser | Glu<br>85 | Asn | Cys | Glu | Glu<br>90 | Phe | Phe | Ile | Pro | Val<br> | Ile<br>95 | Ala |
| Gly | Leu | Phe | Ile<br>100 | Gly | Val | Gly | Val<br>105 | Ala | Pro | Thr | Asn | Glu<br>110 | Ile | Tyr | Thr |
| Leu | Arg | Glu<br>115 | Leu | Val | His | Ser<br>120 | Leu | Gly | Ile | Ser | Lys<br>125 | Pro | Thr | Ile | Val |
| Phe | Ser<br>130 | Ser | Lys | Lys | Gly | Leu<br>135 | Asp | Lys | Val | Ile | Thr<br>140 | Val | Gln | Lys | Thr |
| Val<br>145 | Thr | Thr | Ile | Lys | Thr<br>150 | Ile | Val | Ile | Leu | Asp<br>155 | Ser | Lys | Val | Asp | Tyr<br>160 |
| Arg | Gly | Tyr | Gln | Cys<br>165 | Leu | Asp | Thr | Phe | Ile<br>170 | Lys | Arg | Asn | Thr | Pro<br>175 | Pro |
| Gly | Phe | Gln | Ala<br>180 | Ser | Ser | Phe | Lys | Thr<br>185 | Val | Glu | Val | Asp | Arg<br>190 | Lys | Glu |
| Gln | Val | Ala<br>195 | Leu | Ile | Met | Asn | Ser<br>200 | Ser | Gly | Ser | Thr | Gly<br>205 | Leu | Pro | Lys |
| Gly | Val<br>210 | Gln | Leu | Thr | His | Glu<br>215 | Asn | Thr | Val | Thr | Arg<br>220 | Phe | Ser | His | Ala |
| Arg<br>225 | Asp | Pro | Ile | Tyr | Gly<br>230 | Asn | Gln | Val | Ser | Pro<br>235 | Gly | Thr | Ala | Val | Leu<br>240 |
| Thr | Val | Val | Pro | Phe<br>245 | His | His | Gly | Phe | Gly<br>250 | Met | Phe | Thr | Thr | Leu<br>255 | Gly |
| Tyr | Leu | Ile | Cys<br>260 | Gly | Phe | Arg | Val | Val<br>265 | Met | Leu | Thr | Lys | Phe<br>270 | Asp | Glu |
| Glu | Thr | Phe<br>275 | Leu | Lys | Thr | Leu | Gln<br>280 | Asp | Tyr | Lys | Cys | Thr<br>285 | Ser | Val | Ile |
| Leu | Val<br>290 | Pro | Thr | Leu | Phe | Ala<br>295 | Ile | Leu | Asn | Lys | Ser<br>300 | Glu | Leu | Leu | Asn |
| Lys<br>305 | Tyr | Asp | Leu | Ser | Asn<br>310 | Leu | Val | Glu | Ile | Ala<br>315 | Ser | Gly | Gly | Ala | Pro<br>320 |
| Leu | Ser | Lys | Glu | Val<br>325 | Gly | Glu | Ala | Val | Ala<br>330 | Arg | Arg | Phe | Asn | Leu<br>335 | Pro |
| Gly | Val | Arg | Gln<br>340 | Gly | Tyr | Gly | Leu | Thr<br>345 | Glu | Thr | Thr | Ser | Ala<br>350 | Ile | Ile |
| Ile | Thr | Pro<br>355 | Glu | Gly | Asp | Asp | Lys<br>360 | Pro | Gly | Ala | Ser | Gly<br>365 | Lys | Val | Val |
| Pro | Leu<br>370 | Phe | Lys | Ala | Lys | Val<br>375 | Ile | Asp | Leu | Asp | Thr<br>380 | Lys | Lys | Ser | Leu |
| Gly<br>385 | Pro | Asn | Arg | Arg | Gly<br>390 | Glu | Val | Cys | Val | Lys<br>395 | Gly | Pro | Met | Leu | Met<br>400 |
| Lys | Gly | Tyr | Val | Asn<br>405 | Asn | Pro | Glu | Ala | Thr<br>410 | Lys | Glu | Leu | Ile | Asp<br>415 | Glu |
| Glu | Gly | Trp | Leu<br>420 | His | Thr | Gly | Asp | Ile<br>425 | Gly | Tyr | Tyr | Asp | Glu<br>430 | Glu | Lys |
| His | Phe | Phe<br>435 | Ile | Val | Asp | Arg | Leu<br>440 | Lys | Ser | Leu | Ile | Lys<br>445 | Tyr | Lys | Gly |
| Tyr | Gln<br>450 | Val | Pro | Pro | Ala | Glu<br>455 | Leu | Glu | Ser | Val | Leu<br>460 | Leu | Gln | His | Pro |
| Ser<br>465 | Ile | Phe | Asp | Ala | Gly<br>470 | Val | Ala | Gly | Val | Pro<br>475 | Asp | Pro | Val | Ala | Gly<br>480 |
| Glu | Leu | Pro | Gly | Ala<br>485 | Val | Val | Val | Leu | Glu<br>490 | Ser | Gly | Lys | Asn | Met<br>495 | Thr |
| Glu | Lys | Glu | Val<br>500 | Met | Asp | Tyr | Val | Ala<br>505 | Ser | Gln | Val | Ser | Asn<br>510 | Ala | Lys |

```
Arg Leu Arg Gly Gly Val Arg Phe Val Asp Glu Val Pro Lys Gly Leu
    515                 520                 525

Thr Gly Lys Ile Asp Gly Arg Ala Ile Arg Glu Ile Leu Lys Lys Pro
    530                 535                 540

Val Ala Lys Met
545
```

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGACAATGGA AAACATGGAA AACGATGAAA AT        32

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATTTTCATCG TTTTCCATGT TTTCCATTGT        30